United States Patent
Thomas et al.

(10) Patent No.: US 9,442,064 B1
(45) Date of Patent: Sep. 13, 2016

(54) PHOTOMETER WITH LED LIGHT SOURCE

(71) Applicant: ABB Technology Ltd., Zurich (CH)

(72) Inventors: Thomas J. Thomas, Lewisburg, WV (US); Joanna Radford Kiddle, Lewisburg, WV (US); Gary Brewer, Lewisburg, WV (US); Ronnie Bennett, Clintonville, WV (US)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 14/643,129

(22) Filed: Mar. 10, 2015

(51) Int. Cl.
  *G01N 21/25* (2006.01)
  *G01N 21/31* (2006.01)
  *G01N 21/27* (2006.01)

(52) U.S. Cl.
  CPC .............. *G01N 21/31* (2013.01); *G01N 21/27* (2013.01); *G01N 2201/062* (2013.01)

(58) Field of Classification Search
  CPC ...... G01N 21/31; G01N 21/25; G01N 21/27; G01J 3/02; G01J 3/51; G01J 3/52; G01J 3/50; G01J 3/513
  USPC .................................................. 356/402–425
  See application file for complete search history.

(56) References Cited

U.S. PATENT DOCUMENTS

| | | | |
|---|---|---|---|
| 4,090,792 A | 5/1978 | Bunge | |
| 4,708,477 A | 11/1987 | Kenji et al. | |
| 5,073,029 A | 12/1991 | Eberly et al. | |
| 5,307,146 A | 4/1994 | Porter et al. | |
| 6,097,034 A | 8/2000 | Weckstrom et al. | |
| 6,816,241 B2 | 11/2004 | Grubisic | |
| 7,154,599 B2 | 12/2006 | Adams et al. | |
| 7,259,853 B2 | 8/2007 | Hubble, III et al. | |
| 7,339,657 B2 | 3/2008 | Coates | |
| 8,100,552 B2 | 1/2012 | Spero | |
| 8,184,280 B2 | 5/2012 | Meijer et al. | |
| 8,188,485 B2 | 5/2012 | Schoo et al. | |
| 8,189,196 B2 | 5/2012 | Belz | |
| 8,358,081 B2 | 1/2013 | Panagotacos et al. | |
| 8,766,547 B2 | 7/2014 | Kim | |
| 2003/0010941 A1 | 1/2003 | Spolaczyk et al. | |
| 2007/0037272 A1 | 2/2007 | Beatty et al. | |
| 2009/0080611 A1 | 3/2009 | Ganz et al. | |
| 2011/0108720 A1* | 5/2011 | Ford | E21B 49/08 250/262 |
| 2012/0281389 A1 | 11/2012 | Panagotacos et al. | |
| 2013/8010511 | 11/2013 | Pogosyan et al. | |
| 2014/0168989 A1 | 6/2014 | Van De Ven et al. | |

FOREIGN PATENT DOCUMENTS

EP       0194005 A1    10/1986

OTHER PUBLICATIONS

ABB Inc., "ABB Models PIR3502 and PUV3402 Process Photometers in the EDC/VCM Process" The Analyzer, Powerpoint, Feb. 19, 2003; 23 pages, Lewisburg, WV.
ABB Inc., "PUV3402, PIR3502 and PF03372 process photometers Applications, technology and data" Brochure, copyright 2013, 12 pages, Lewisburg, WV.
International Search Report and Written Opinion, PCT/US2016/021541, mailed May 16, 2016, ASB Technology AG, 14 pgs.

\* cited by examiner

*Primary Examiner* — Abdullahi Nur
(74) *Attorney, Agent, or Firm* — Taft Stettinius & Hollister LLP

(57) ABSTRACT

A photometer is provided for measuring the concentration of a chromophore in a fluid. The photometer includes a light source, a sample cell and a detector. The light source includes first, second, third and fourth light emitting diodes (LEDs). Each of the first and second LEDs emit light at a measurement wavelength and each of the third and fourth LEDs emit light at a reference wavelength. The first and second LEDs are arranged diagonal to each other and the third and fourth LEDs are arranged diagonal to each other. The photometer performs a routine for correcting concentration measurement for LED drift.

17 Claims, 6 Drawing Sheets

PHOTOMETER WITH LED LIGHT SOURCE

BACKGROUND OF THE INVENTION

The present invention relates to photometers and more particularly to a photometer with an improved light source.

A photometer is a device used to measure the concentration of a component (chromophore) in a fluid (gas or liquid) by determining the absorbance of a specific wavelength of light by the chromophore. The concentration of the chromophore is determined from the measured absorbance through the Beer-Lambert relationship: A=ebc where A=absorbance, e=chromophore absorptivity, b=pathlength, and c=chromophore concentration.

One of the most common conventional photometers is a Sigrist photometer, which includes a light source, a filter wheel, a sample cell and a photoreceiver or detector. The light source generates a continuous beam of electromagnetic radiation (light) that follows an optical path that extends through lenses, passes through the filter wheel, travels through the sample cell and impinges on the detector. The filter wheel includes a reference filter and a measure filter. The reference filter is operable to isolate the light beam to a reference wavelength, while the measure filter is operable to isolate the light beam to a measure wavelength. The reference wavelength is one in which the chromophore has little or no absorption, while the measure wavelength is the one in which the chromophore absorbs energy. A chopper motor rotates the filter wheel to alternately pass the reference filter and the measure filter through the light beam, thereby converting the light beam into alternating measurement and reference beams.

From the filter wheel, the measurement and reference beams pass through a lens where they are collimated before passing through the sample cell. The beams exit the sample cell and are focused on the detector by another lens. The detector converts the beams into voltage signals proportional to the light intensity received by the detector. An electronics assembly calculates a ratio of the intensities of the measurement and reference beams, which eliminates errors resulting from luminosity fluctuations of the light source and any changes in the detector sensitivity. This transmittance ratio is then used by the electronics assembly to determine absorbance, which is the negative logarithm of transmittance. The absorbance, in turn, is used to calculate the concentration of the chromophore.

The light source for a photometer must generate a light beam that is sufficiently powerful for easy detection and measurement. In addition, its output power should be stable for reasonable periods. Light sources can be a continuum source, which emits radiation that changes in intensity only slowly as a function of wavelength, or a line source, which emits a limited number of spectral lines. Commonly used continuum light sources include tungsten/halogen lamps and deuterium lamps. A typical tungsten/halogen lamp provides a distribution of wavelengths from 320 to 2500 nm, while a typical deuterium lamp provides a distribution of wavelengths about 160 nm to about 350 to 400 nm. Both tungsten/halogen and deuterium lamps operate at high temperatures and consume a large amount of electric power. Moreover, the filter wheel and chopper motor introduce complexity into the operation of the photometer.

The present invention is directed to an improved photometer that addresses these issues.

SUMMARY OF THE INVENTION

In accordance with the present invention, a photometer is provided for measuring the concentration of a chromophore in a fluid. The chromophore absorbs light at a measurement wavelength and absorbs substantially less light at a reference wavelength. The photometer includes a light source having first, second, third and fourth light emitting diodes (LEDs). Each of the first and second LEDs are operable to generate measurement light at the measurement wavelength and each of the third and fourth LEDs are operable to generate reference light at the reference wavelength. The measurement light and the reference light follow an optical path. A sample cell holds the fluid and is positioned relative to the light source such that the optical path passes through the sample cell. A detector is arranged to receive the reference light and the measurement light after having passed through the sample cell. The detector generates at least one signal proportional to the intensity of the reference light and the measurement light received. Centers of the first and second LEDs are respectively arranged in diagonal first and second quadrants defined by perpendicular first and second axes.

Also provided in accordance with the present invention is a method of measuring the concentration of a chromophore in a fluid. The chromophore absorbs light at a measurement wavelength and absorbs substantially less light at a reference wavelength. In accordance with the method, the fluid with the chromaphore is placed in a sample cell through which an optical path extends. Measurement light at the measurement wavelength is generated from first and second light emitting diodes (LEDs) positioned diagonal to each other. The measurement light travels along the optical path. Reference light at the reference wavelength is generated from third and fourth LEDs positioned diagonal to each other. The reference light travels along the optical path. After having passed through the sample cell containing the chromopore, the reference light is received. After having passed through the sample cell containing the chromopore, the measurement light is received. A reference signal proportional to the intensity of the reference light received is generated. A measurement signal proportional to the intensity of the measurement light received is generated. The concentration of the chromophore is determined from the measurement and reference signals.

BRIEF DESCRIPTION OF THE DRAWINGS

The features, aspects, and advantages of the present invention will become better understood with regard to the following description, appended claims, and accompanying drawings where:

DETAILED DESCRIPTION OF ILLUSTRATIVE EMBODIMENTS

Figure 1:
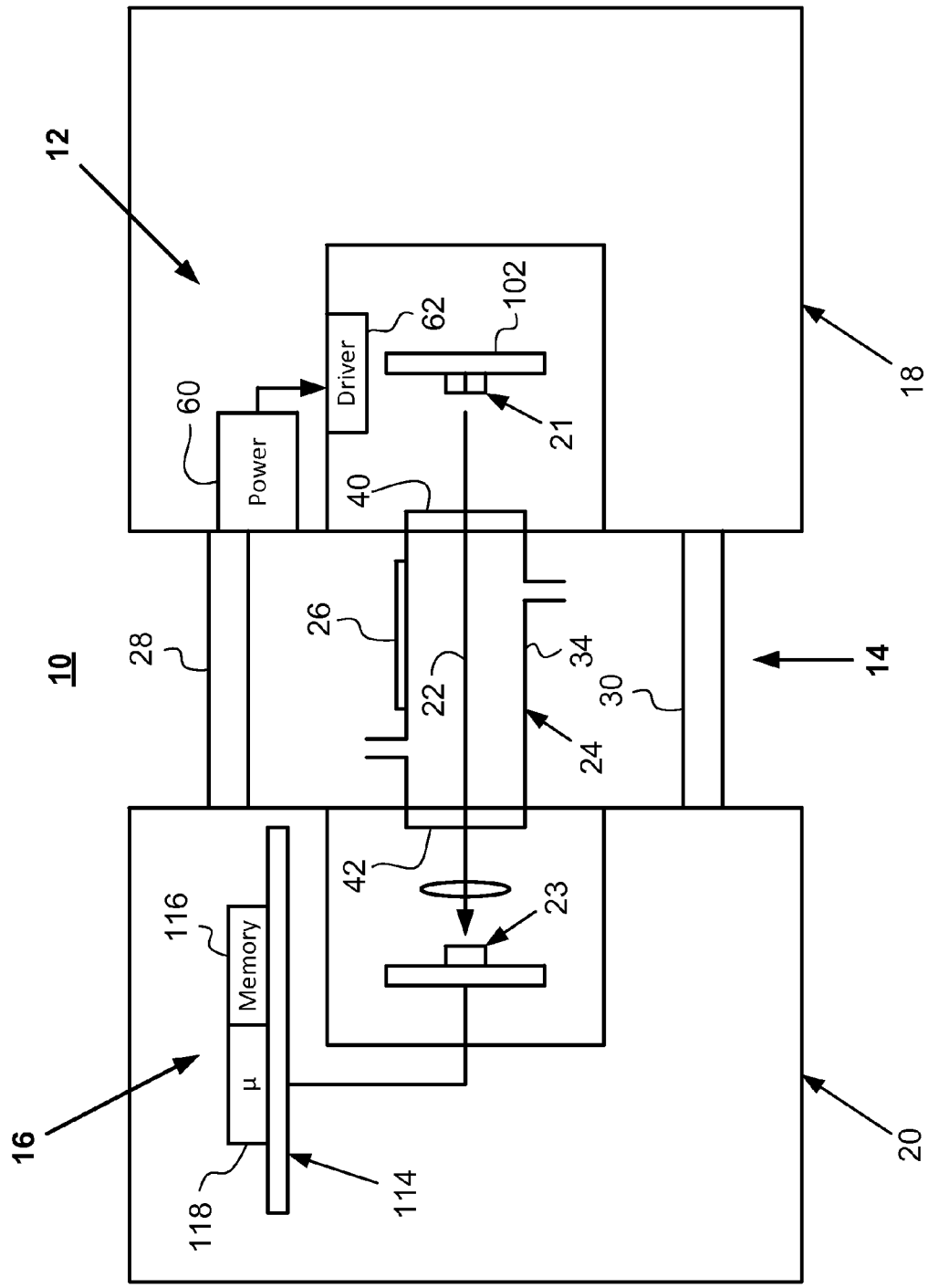
FIG. 1 shows a schematic diagram of a photometer.

It should be noted that in the detailed description that follows, identical components have the same reference numerals, regardless of whether they are shown in different embodiments of the present invention. It should also be noted that in order to clearly and concisely disclose the present invention, the drawings may not necessarily be to scale and certain features of the invention may be shown in somewhat schematic form.

Referring now to FIG. 1, there is shown a photometer 10 constructed in accordance with the present invention. The photometer 10 is an on-line process photometer that is adapted for measuring the concentration of one or more compounds (chromophores) of interest. In some embodiments of the present invention, the photometer 10 is adapted to measure the concentration of only one or a group of chromophores, without modifying the photometer 10, as will be discussed more fully below. However, in other embodiments of the present invention, the photometer is adapted to measure the concentration of a plurality of chromophores or groups of chromophores, as will also be discussed more fully below. It should be appreciated that while the photometer 10 is described as being an on-line process photometer, the present invention is not limited to this type of photometer. For example, the present invention may be embodied in a portable field photometer or a laboratory photometer.

The photometer 10 includes a light source assembly 12, a sample cell assembly 14 and a detector assembly 16. The light source assembly 12 and the detector assembly 16 may be mounted in separate enclosures. For example, the light source assembly 12 may be mounted in an enclosure 18, while the detector assembly 16 may be mounted in an enclosure 20. The sample cell assembly 14 may be mounted and extend in between the enclosure 18 and the enclosure 20. An optical path 22 extends between a first light source 21 of the light source assembly 12 and a detector 23 of the detector assembly 16. As will be described more fully below, light travels from the first light source 21, over the optical path 22, to the detector 23.

The sample cell assembly 14 includes a sample cell 24, an optional heater 26 and upper and lower stabilizer (tie) rods 28, 30. The sample cell assembly 14 is isolated from the electronics in the source assembly 12 and the detector assembly 16. This isolation allows easy access to the sample lines, simplifies routine maintenance procedures, reduces radiant heat effects from heated sample streams, and allows the sample cell 24 to be heated by the heater 26 to high temperatures (e.g., 150° C.) without harming the electronic components of the photometer 10. The upper and lower stabilizer rods 28, 30 provide optical self-alignment during maintenance. The sample cell 24 is tubular and includes an outer casing 34 with an inlet and an outlet for connection to a source of sample fluid from a process. The sample fluid contains one or more chromophores of interest whose concentration is to be measured. The casing 34 may be composed of stainless steel and is in thermal and/or physical contact with the heater 26. Windows 40, 42 are mounted toward opposing ends of the casing 34. The windows 40, 42 are composed of a transparent material, such as quartz or sapphire glass. The casing 34, windows 40, 42 and all seals are compatible with both the chemical and physical properties of the sample fluid being analyzed.

Figure 2:
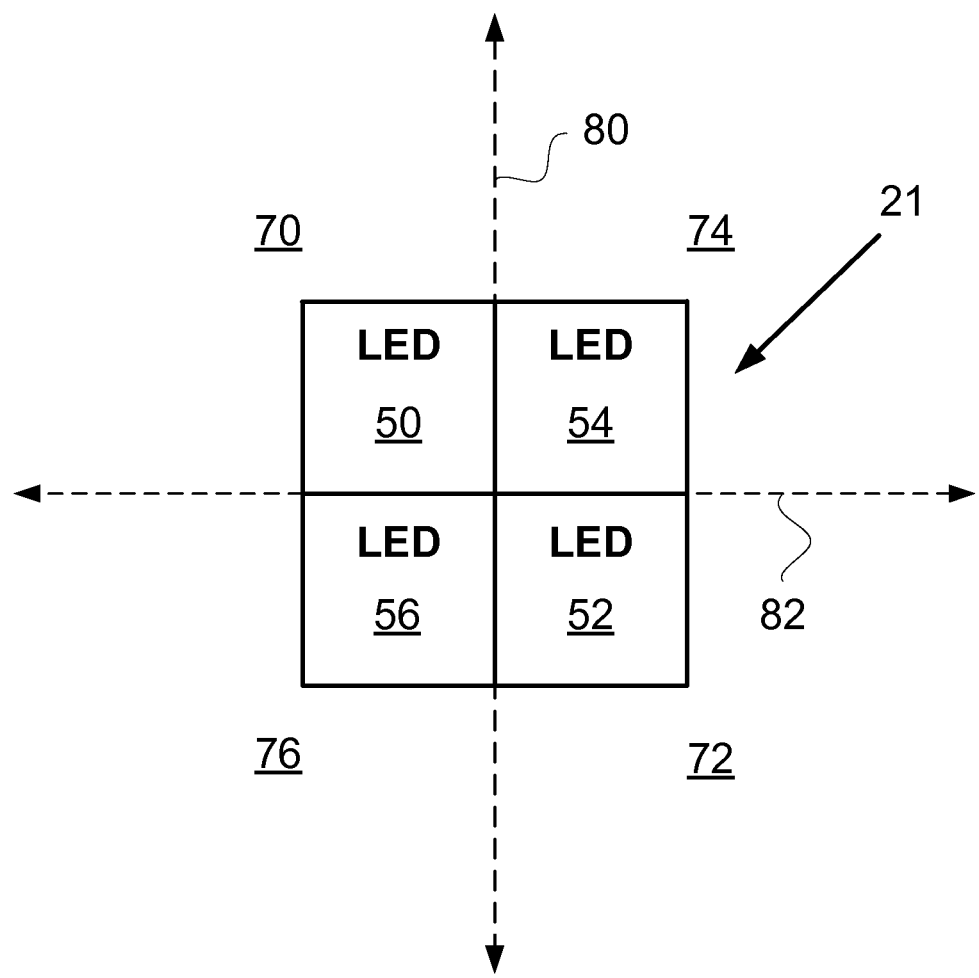
FIG. 2 shows a schematic diagram of a first light source of the photometer, the first light source being constructed in accordance with a first embodiment of the present invention.

Referring now also to FIG. 2, a schematic rendition of the first light source 21 is shown. The first light source 21 comprises a first light emitting diode (LED) 50, a second LED 52, a third LED 54 and a fourth LED 56. The light source assembly 12 further includes a power source 60 and a driver 62. The driver 62 controls the supply of power to the LEDs 50-56. The first and second LEDs 50, 52 each emit light at a wavelength the chromophore strongly absorbs. The third and fourth LEDs 54, 56 each emit light at a wavelength the chromophore does not absorb or absorbs minimally. The first, second, third and fourth LEDs 50-56 are positioned to emit light in a direction perpendicular to an emission plane having four quadrants 70, 72, 74, 76 defined by first and second axes 80, 82 that are arranged perpendicular to each other. Centers of the first, second, third and fourth LEDs 50-56 are disposed in the first, second, third and fourth quadrants 70-76, respectively. The first and second quadrants 70, 72, which contain the first and second LEDs 50, 52 respectively, are diagonal to each other. Similarly, the third and fourth quadrants 74, 76, which contain the third and fourth LEDs 54, 56 respectively, are diagonal to each other. In this manner, the first and second LEDs 50, 52 are diagonal to each other and the third and fourth LEDs 54, 56 are diagonal to each other. It is desirable for the first, second, third and fourth LEDs 50-56 to be arranged proximate to each other, i.e., the distance between each LED and each of the other LEDs is less than the greatest dimension of each of the LEDs in the emission plane. More specifically, it is desirable if the first, second, third and fourth LEDs 50-56 are as close as possible to each other. In this manner, the first, second, third and fourth LEDs 50-56 generally form a rectangle and more specifically, a square. With this arrangement, individual measure light beams 90, 92 (shown in FIGS. 7 and 8) emitted by the first and second LEDs 50, 52, respectively, are contiguous or close together so as to create a composite measure light beam. Similarly, individual reference light beams 94, 96 emitted by the third and fourth LEDs 54, 56, respectively, are contiguous or close together so as to create a composite reference light beam.

Figure 3:
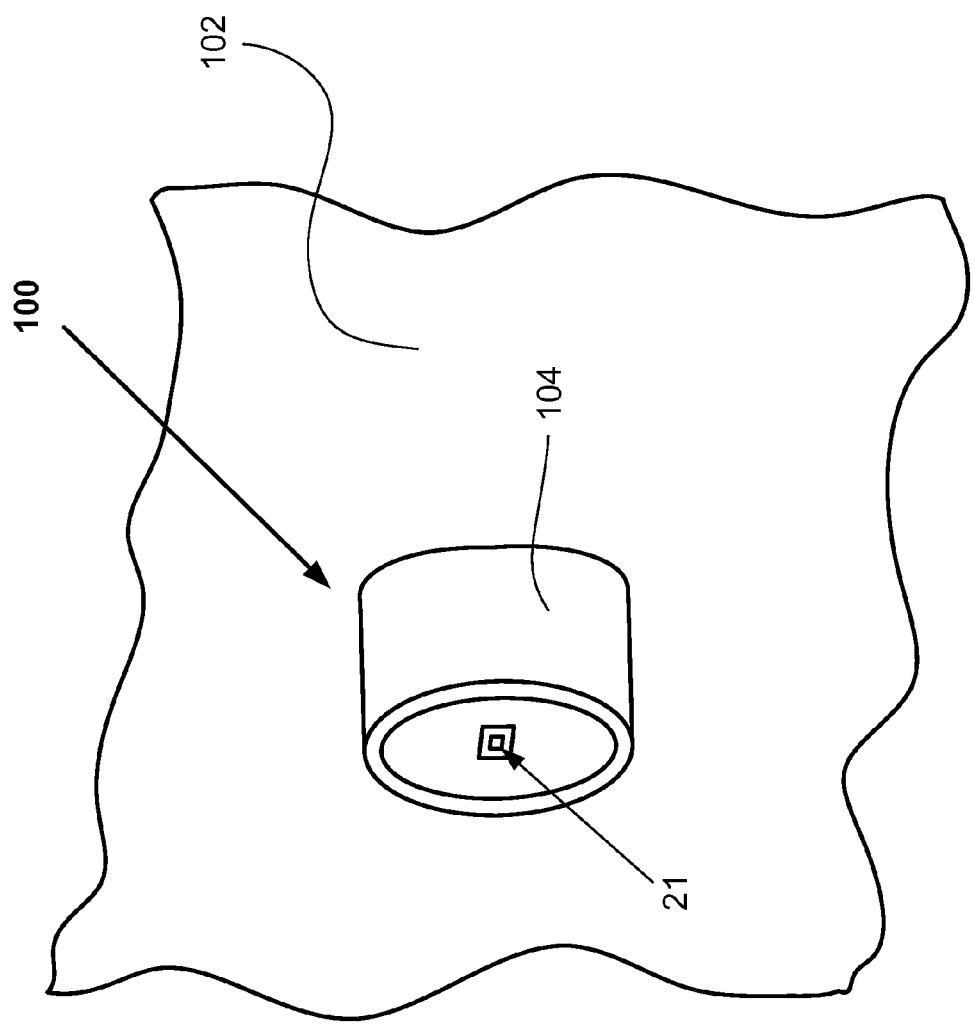
FIG. 3 shows a schematic diagram of a solid state embodiment of the first light source.

The first light source 21 may be mounted in a single integrated circuit package 100, which, in turn, is mounted to a source circuit board 102. More specifically, the integrated circuit package 100 may be a TO-8 package having a cylindrical housing 104 with a diameter of less than half an inch. As shown in FIG. 3, the first light source 21 is small and mounted toward the center of the housing 104.

As set forth above, the first and second LEDs 50, 52 each emit light at a wavelength the chromophore strongly absorbs. In one non-limiting embodiment, the first and second LEDs 50, 52 emit light at a wavelength of 280 nm, while the third and fourth LEDs 54, 56 emit light at a wavelength of 320 nm. In this embodiment, the chromophore is sulfur dioxide, which strongly absorbs light at 280 nm (measurement wavelength), but not at 320 nm (reference wavelength). In another non-limiting embodiment, the first and second LEDs 50, 52 emit light at a wavelength of 255 nm (measurement wavelength), while the third and fourth LEDs 54, 56 emit light at a wavelength of 320 nm (reference wavelength). In this embodiment, the chromophore is an aromatic, which strongly absorbs light at 255 nm, but not at 320 nm. It should be appreciated that the LEDs 50-56 may have other combinations of (measurement and reference wavelengths), depending on the chromophore whose concentration is being measured.

The photometer 10 may be manufactured for measuring the concentration of a specific chromophore or group of chromophores. In this manner, the specific types (wavelengths) of the LEDs 50-56 that are used in the photometer 10 are determined in the factory based upon the chromophore(s) for which the photometer 10 is being manufactured. However, the photometer 10 may be adapted to measure different chromophores or groups of chromophores by being constructed to permit the LEDs 50-56 to be facilely changed outside of the factory, such as in the field or laboratory. This change may be performed by removing the source circuit board 102 containing a first set of LEDs and replacing it with another source circuit board containing a second set of different LEDs. Alternately, different sets of LEDs may be mounted on a structure (such as a wheel) that may be moved to selectively place a set of LEDs in a position to create the reference and measure light beams for travel along the optical path 22. Still another construction is described below with regard to FIG. 9.

When the concentration of the chromophore in a fluid is being measured, the light source assembly 12 operates to first turn on (provide power to) the third and fourth LEDs 54, 56 so as to generate reference light beams 94, 96 (shown in FIGS. 7 and 8), which travel along the optical path 22, through the sample cell 24 containing the fluid and then on to the detector assembly 16. The third and fourth LEDs 54, 56 are then turned off. Next, the first and second LEDs 50, 52 are turned on so as to generate measure light beams 90, 92 (shown in FIGS. 7 and 8), which also travel along the optical path 22, through the sample cell 24 containing the fluid and then on to the detector assembly 16. The first and second LEDs 50, 52 are then turned off. The on-off operation of the LEDs 50-56 is controlled by the driver 62.

Referring back to FIG. 1, the detector assembly 16 includes the detector 23, which has a solid-state construction that is insensitive to external vibrations and mechanical shock. The detector 23 is operable to measure the range of wavelengths generated by the source assembly 12. In one embodiment, the detector 23 is operable to measure light in the 200 to 800 nanometer wavelength range. The detector 23 alternately receives the reference light beams 94, 96 and the measure light beams 90, 92 and generates signals in proportion to the light intensity received by the detector 23. A calculation/control PCB (printed circuit board) 114 receives the signals from the detector 23 and calculates the concentration of the chromophore therefrom. The calculation/control PCB 114 includes memory 116 and a microprocessor 118 (with an associated clock) operable to calculate the component concentration using the Beer-Lambert relationship described above. In calculating the concentration, a ratio of the light received from the measure light beams 90, 92 and the reference light beams 94, 96 (really the signals corresponding thereto) is used to remove any changes in luminosity fluctuations (any spectrally-neutral phenomenon such as a spectrally-neutral obscuration or diminishing of the beam, or spectrally-neutral changes in intensity of the source or sensitivity of the detector) and detector sensitivity as sources of error.

While using the ratio of light received from the measure and reference light beams 90-96 removes some sources of error, it does not remove error caused by drift of the LEDs 50-56. LEDs exhibit a decay that is seen as drift when the LEDs are used as a photometer light source. The drift is wavelength-specific, so LEDs with the same wavelength will exhibit the same drift at similar conditions (temperature and driving current or voltage). As such, the first and second LEDs 50, 52 will have a different drift than the third and fourth LEDs 54, 56. Thus, when the light detected from the reference light beams 94, 96 and the measure light beams 90, 92 are compared, a drifting baseline is observed. Applicants have noticed that when observed over relatively short periods of time (such as up to 90 days), the drift in the baseline is approximately linear. This observation is utilized by a routine 120 that stabilizes the baseline and provides more accurate measurements.

Figure 4:
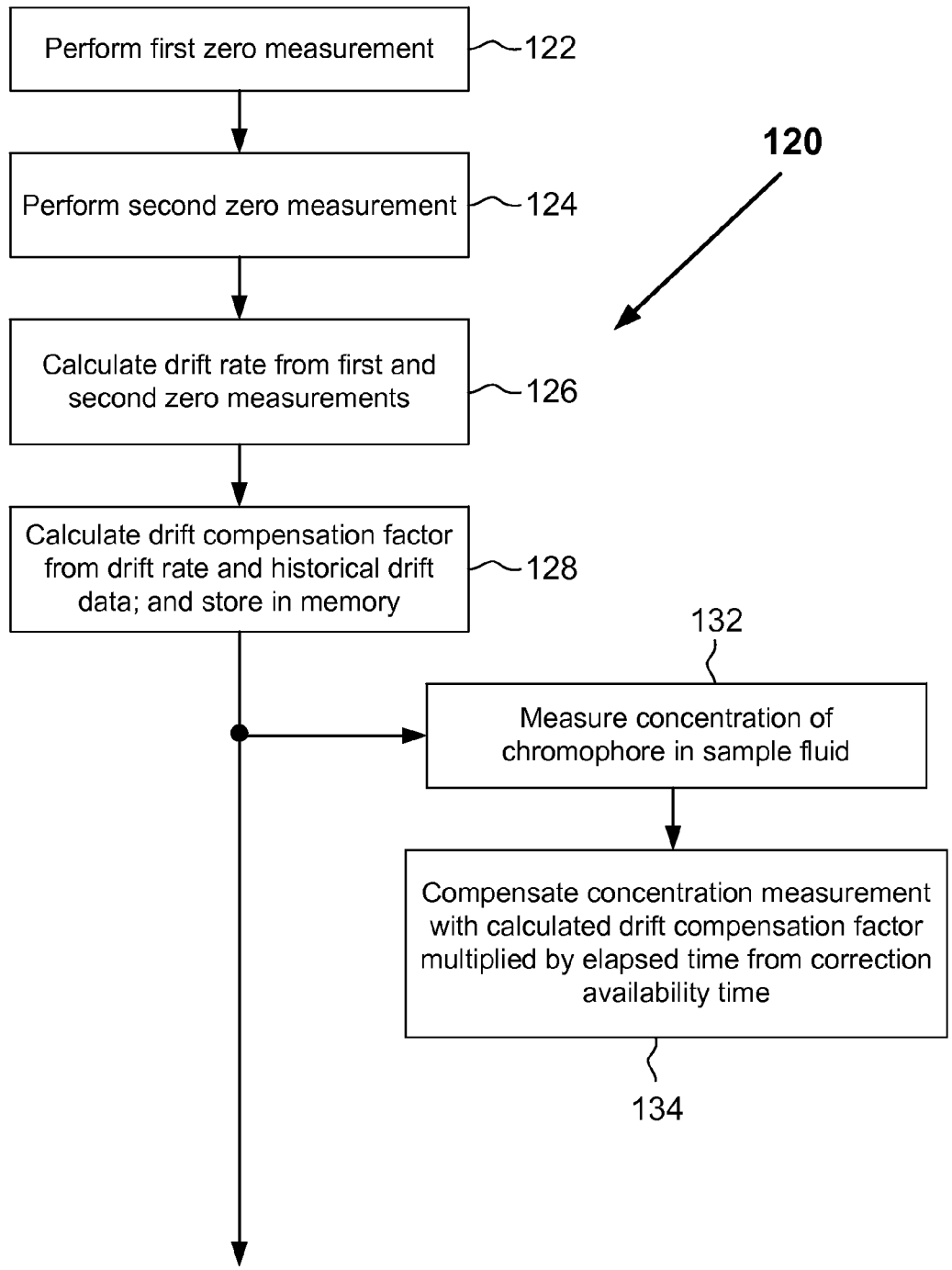
FIG. 4 shows a flow diagram of a routine for correcting concentration measurement for LED drift.

Referring now to FIG. 4, the routine 120 begins at step 122, wherein a zero sample having no absorption at both the measure and reference wavelengths is placed in the sample cell 24 and the zero absorbance is measured. In step 124, at a measure time period later (such as 1, 5 or 30 days), the zero sample is again placed in the sample cell 24 and the zero absorbance is measured again. The zero or baseline drift rate is calculated in step 126 by subtracting the zero measurements and dividing by the time interval between measurements (the measure time period). In step 128, the drift rate and historical drift data are used to calculate a drift compensation factor which is then stored in memory 116. The time at which the drift compensation factor is stored in memory 116 (and available for use) shall be referred to as the "correction availability time". The concentration of a chromophore in a sample fluid may be measured in step 132 by placing the sample fluid in the sample cell 24, operating the first light source 21 as described above and calculating the concentration using the signals from the detector 23. In step 134, the microprocessor 118 uses the drift compensation factor to correct the concentration to account for LED drift. More specifically, the drift compensation factor is multiplied by the amount of time that has elapsed from the correction availability time and is applied to (added/subtracted to/from) the concentration measurement. Thereafter, the routine 120 remains available to provide drift corrections to concentration measurements.

At any time, a new drift compensation factor may be calculated by re-performing steps 122 through 128. In such an event, while steps 122-128 are being re-performed, the routine 120 remains available (except when the zero samples are being measured) to provide drift corrections to concentration measurements using the current drift compensation factor. However, once a new drift compensation factor is calculated, the routine 120 uses the new drift compensation factor to provide corrections to concentration measurements. If the routine 120 is fully automated, the routine 120 may automatically branch off and re-perform steps 122-128 at intervals as determined by the demands of the application or the user. In this regard, it should be appreciated that the routine 120 may be fully automated (no steps performed by an operator) or may be partially automated (some steps are performed by an operator).

It is advantageous if steps 122-128 are performed on a fixed schedule under the same operating conditions for the photometer 10 (e.g, the same temperature, pressure, etc.). By performing steps 122-128 on a regular schedule, the baseline will trend with the LEDs' decay. The measurement times are selected such that diurnal or other cyclic or noncyclic effects have no influence on the ratio, and care is taken to extend the measurement interval so that noise will not inflate the projected baseline rate.

The arrangement of the light beams 90-96 helps mitigate the effects of a physical shift in the optical path 22, which can impact the amount of light that reaches the detector 23. More specifically, the diagonal placement (relative to each other) of the first and second LEDs 50, 52 and the diagonal placement (relative to each other) of the third and fourth LEDs 54, 56 reduces the effects of a physical shift in both x and y dimensions of the optical path 22. The benefits of the diagonal arrangement of the two pairs of LEDs can best be appreciated with reference to FIGS. 5 and 6, which schematically show features of a second light source with a single reference LED and a single measure LED, and FIGS. 7 and 8, which schematically show features of the first light source 21 of the present invention. The second light source is not embodied in accordance with the present invention, but for purposes of discussion, will be assumed to be installed in the photometer 10.

Figure 5:
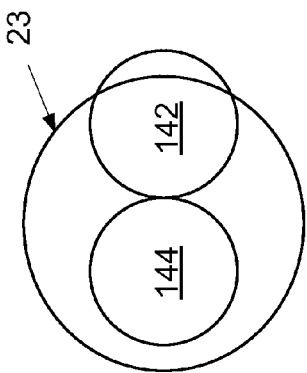
FIG. 5 shows a schematic of light beams from a second light source of the photometer impinging on the detector when the photometer's optical path is in alignment.
Figure 6:
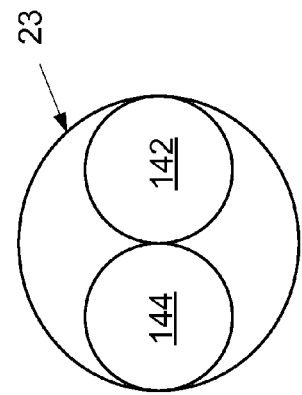
FIG. 6 shows a schematic of the light beams from the second light source impinging on the detector when the photometer's optical path is out of alignment.

In FIG. 5, a reference light beam 142 from the single reference LED of the second light source and a measure light beam 144 from the single measure LED of the second light source are schematically shown impinging on the detector 23 when the optical path is correctly positioned, i.e., the second light source and the detector 23 are properly aligned. As is shown, the detector 23 receives all of the reference light beam 142 and all of the measure light beam 144. In FIG. 6, the optical path has shifted in the X direction so that the detector 23 and the second light source are no longer aligned. As shown, the detector 23 receives all of the measure light beam 144, but not all of the reference light beam 142. As a result, an error is introduced into the concentration measurement because the ratio between the measure light and reference light received at the detector 23 is changed due to the shift in the optical path.

Figure 7:
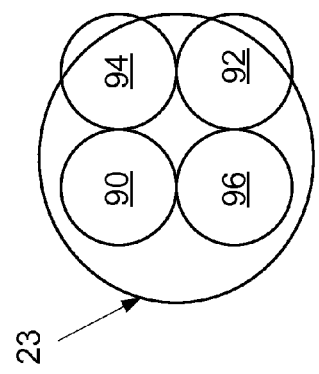
FIG. 7 shows a schematic of light beams from the first light source impinging on the detector when the photometer's optical path is in alignment.
Figure 8:
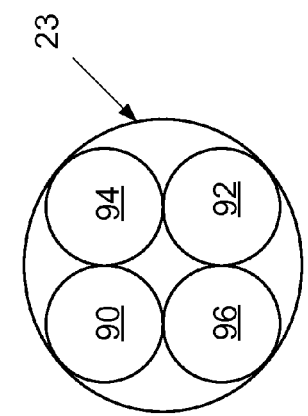
FIG. 8 shows a schematic of the light beams from the first light source impinging on the detector when the photometer's optical path is out of alignment.

Referring now to FIG. 7, the reference light beams 94, 96 from the third and fourth LEDs 54, 56 and the measure light beams 90, 92 from the first and second LEDs 50, 52 of the first light source 21 are schematically shown impinging on the detector 23 when the optical path 22 is correctly positioned, i.e., the first light source 21 and the detector 23 are properly aligned. As is shown, the detector 23 receives all of the measure light beams 90-92 and all of the reference light beams 94-96. In FIG. 8, the optical path 22 has shifted in the X direction so that the detector 23 and the first light source 21 are no longer aligned. As shown, the detector 23 receives all of the measure light beam 90 from the first LED 50 and all of the reference light beam 96 from the fourth LED 56. However, the detector 23 does not receive all of the measure light beam 92 of the second LED 52 and does not receive all of the reference light beam 94 from the third LED 54. However, due to the diagonal arrangement of the pairs of LEDs, the proportion of the measure light beam 92 received is about the same as the proportion of the reference light beam 94 received. Thus, the ratio between the total amount of light received from the measure light beams and the reference light beam is not changed due to the shift in optical path 22. As such, no error is introduced into the concentration measurement.

Figure 9:
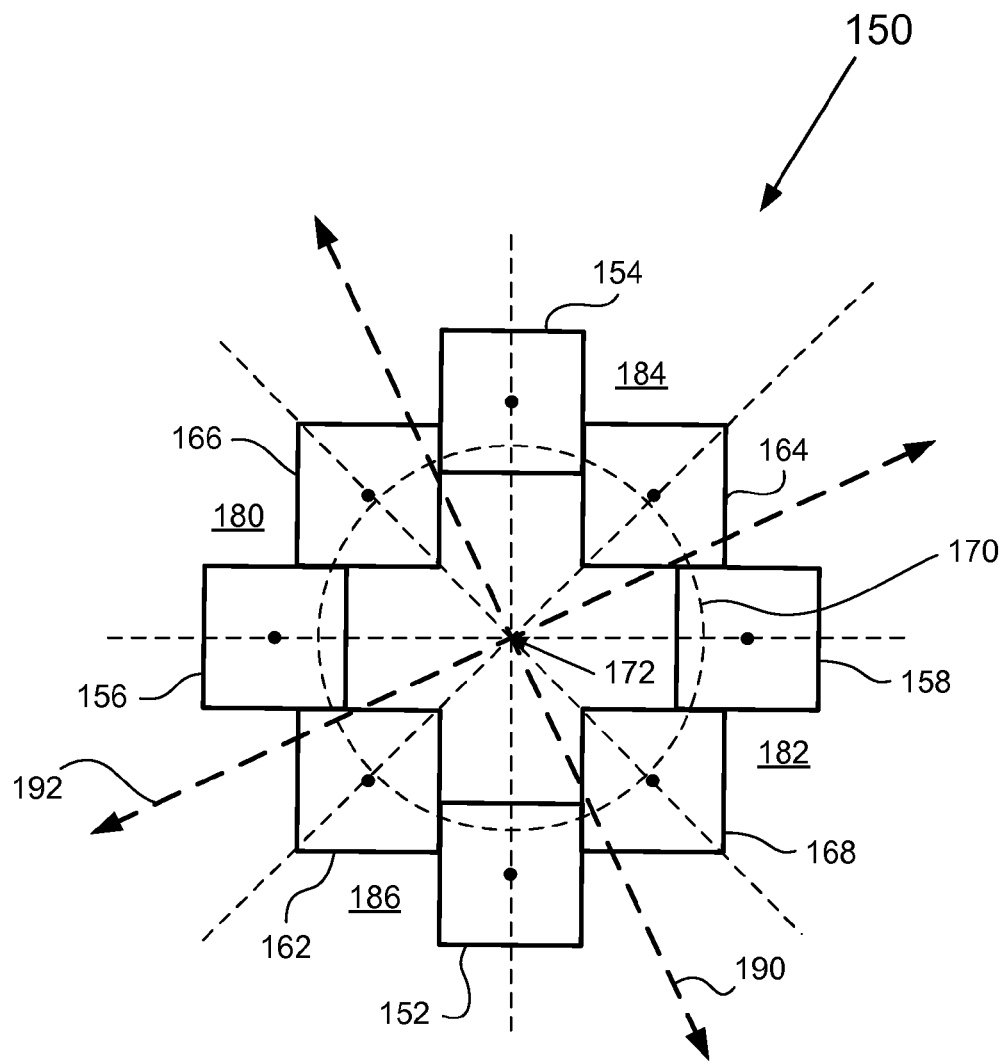
FIG. 9 shows a schematic diagram of a third light source of the photometer, the third light source being constructed in accordance with a second embodiment of the present invention.

Referring now to FIG. 9, there is shown a schematic rendition of a third light source 150 constructed in accordance with a second embodiment of the present invention. The third light source 150 may be used in the photometer 10 in lieu of the first light source 21. Like the first light source 21, the third light source 150 may be mounted in a single integrated circuit package, which, in turn, is mounted to the source circuit board 102. The integrated circuit package may also be a TO-8 package. The third light source 150 is operable to produce light at different wavelengths to measure the concentration of a plurality of different chromophores or to correct for spectral interferences on a measurement. The third light source 150 comprises a plurality of LEDs 152, 154, 156, 158, 162, 164, 166, 168 arranged around a circle 170 having a center 172. The circle 170 encompasses portions of four quadrants 180, 182, 184, 186 defined by two perpendicular axes 190, 192, intersecting at the center 172 of the circle 170. The LEDs 152-168 are arranged in pairs of radially-aligned LEDs, e.g., LEDs 152, 154; LEDs 156, 158; LEDs 162, 164; and LEDs 166, 168. The LEDs in each pair emit light at the same wavelength. In addition, centers of the LEDs in each pair are located in diagonally-oriented quadrants. Thus, the center of LED 152 is located in quadrant 186, which is diagonal to quadrant 184, which contains the center of LED 154.

The LED pairs include at least two pairs of LEDs that emit light at wavelengths strongly absorbed by two different chromophores or group of chromophores, i.e., are measurement LEDs. In addition, at least one pair of the LEDs emit light at a wavelength that is not absorbed or is weakly absorbed by at least one of the chromophores, i.e., are reference LEDs. The number of reference LED pairs in the third light source 150 is dependent on the chromophores or groups of chromophores that are being measured. For example, two or more pairs of measurement LEDs may share a single pair of reference LEDs. Alternately, each pair of measurement LEDs may have its own associated pair of reference LEDs. Preferably, a pair of measurement LEDs is close to its associated pair of reference LEDs.

In a first exemplary construction, LEDs 152, 154 are measurement LEDs that each emit light having a measurement wavelength "a1". The LEDs 156, 158 are also measurement LEDs and each emit light having a measurement wavelength "a2", which is different from the measurement wavelength "a1". LEDs 162, 164 are reference LEDs that each emit light having a reference wavelength "b". The wavelength "a1" emitted by the LEDs 152, 154 is strongly absorbed by a first chromophore, while the wavelength "b" emitted the LEDs 162, 164 is not absorbed or weakly absorbed by the first chromophore. The wavelength "a2" emitted by the LEDs 156, 158 is strongly absorbed by a second chromophore, while the wavelength "b" emitted by the LEDs 162, 164 is not absorbed or weakly absorbed by the second chromophore. Thus, in the first exemplary construction, the pair of LEDs 152, 154 and the pair of LEDs 156, 158, which are measurement LEDs share the pair of LEDs 162, 164, which are reference LEDs.

A second exemplary construction has the same construction as the first exemplary construction, except LEDs 162, 164 emit light having a reference wavelength "b1" which is not absorbed or weakly absorbed by the first chromophore. However, the reference wavelength "b1" is absorbed by the second chromophore. Thus, the LEDs 166, 168 are used as reference LEDs for the second chromophore. The LEDs 166, 168 emit light having a reference wavelength "b2", which is not absorbed or weakly absorbed by the second chromophore. Thus, in the second exemplary construction, the LEDs 162, 164 are reference LEDs that are only associated with the LEDs 152, 154, which are measurement LEDs, and LEDs 166, 168 are reference LEDs that are only associated with the LEDs 156, 158, which are measurement LEDs.

When the concentrations of the first and second chromophores in a fluid are being measured using the second exemplary construction of the third light source 150, the light source assembly 12 (with the third light source 150) operates to first turn on (provide power to) the LEDs 162, 164 so as to generate first reference light beams, which travel along the optical path 22, through the sample cell 24 containing the fluid and then on to the detector assembly 16. The LEDs 162, 164 are then turned off. Next, the LEDs 152, 154 are turned on so as to generate first measure light beams, which also travel along the optical path 22, through the sample cell 24 containing the fluid and then on to the detector assembly 16. The LEDs 152, 154 are then turned off. The concentration of the first chromophore is then calculated using signals generated by the detector 23 proportional to the light intensity received by the detector 23 from the first reference and measure light beams. The LEDs 166, 168 are then turned on so as to generate second reference light beams, which travel along the optical path 22, through the sample cell 24 containing the fluid and then on to the detector assembly 16. The LEDs 166, 168 are then turned off. Next, the LEDs 156, 158 are turned on so as to generate second measure light beams, which also travel along the optical path 22, through the sample cell 24 containing the fluid and then on to the detector assembly 16. The LEDs 156, 158 are then turned off. The concentration of the second chromophore is then calculated using signals generated by the detector 23 proportional to the light intensity received by the detector 23 from the second reference and measure light beams. The foregoing procedure is continuously repeated so that the concentrations of the first and second chromophores are continuously determined and made available to an operator. It should be appreciated that the procedure for measuring the first and second chromophores in the fluid using the first exemplary construction of the third light source 150 is the same as that described above for the second exemplary construction, except that the LEDs 162, 164 (instead of the LEDs 166, 168) are turned on and off before the LEDs 156, 158 are turned on and off.

It should be appreciated that the third light source 150 may be modified to include LEDs in addition to the LEDs 152-168. The additional LEDs are also arranged in pairs and are disposed around a circle, which is of greater diameter than the circle 170 so as to accommodate the additional LEDs. Within each pair, the LEDs are radially aligned. The additional LEDs may permit the concentration of an additional one, two, three or more chromophores or groups of chromophores to be measured. The LEDs are arranged to adjoin or otherwise be close to each other.

It is to be understood that the description of the foregoing exemplary embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A photometer for measuring the concentration of a chromophore in a fluid, the chromophore absorbing light at a measurement wavelength and absorbing substantially less light at a reference wavelength, the photometer comprising:
   a light source including first, second, third and fourth light emitting diodes (LEDs), each of the first and second LEDs being operable to generate measurement light at the measurement wavelength and each of the third and fourth LEDs operable to generate reference light at the reference wavelength, the measurement light and the reference light following an optical path;
   a sample cell for holding the fluid, the sample cell being positioned relative to the light source such that the optical path passes through the sample cell; a heating system in thermal communication with the sample cell;
   a detector arranged to receive the reference light and the measurement light after having passed through the sample cell, the detector generating at least one signal proportional to the intensity of the reference light and the measurement light received; and
   wherein centers of the first and second LEDs are respectively arranged in diagonal first and second quadrants defined by perpendicular first and second axes.

2. The photometer of claim 1, wherein the light source alternately generates the measurement light and the reference light, and wherein the at least one signal generated by the detector comprises a measurement signal proportional to the measurement light received and a reference signal proportional to the reference light received.

3. The photometer of claim 2, wherein the photometer further comprises a microprocessor that receives the measurement and reference signals generated by the detector and calculates the concentration of the chromophore therefrom.

4. The photometer of claim 2, wherein the chromophore is a first chromophore and the measurement light is a first measurement light; and
   wherein the photometer is also operable to measure the concentration of a second chromophore in the fluid, the second chromophore absorbing light at a second measurement wavelength, and wherein the photometer further comprises fifth and sixth LEDs each of which is operable to generate second measurement light at the second measurement wavelength.

5. The photometer of claim 4, wherein the photometer is operable to sequentially and repeatedly measure the concentrations of the first and second chromophores.

6. The photometer of claim 4, wherein the measurement signal is a first measurement signal and the detector is arranged to receive the second measurement light after having passed through the sample cell, the detector generating a second measurement signal proportional to the intensity of the second measurement light received.

7. The photometer of claim 6, wherein the second chromophore absorbs substantially less light at the reference wavelength; and
   wherein the photometer further comprises a microprocessor that receives the second measurement signal and the reference signal generated by the detector and calculates the concentration of the second chromophore therefrom.

8. The photometer of claim 6, wherein the reference light is a first reference light; and
   wherein the photometer further comprises seventh and eighth LEDs each of which is operable to generate a second reference light at the second reference wavelength, the second chromophore absorbing less light at the second reference wavelength than at the second measurement wavelength.

9. The photometer of claim 8, wherein the detector is arranged to receive the second reference light after having passed through the sample cell, the detector generating a second reference signal proportional to the intensity of the second reference light received; and
   wherein the photometer further comprises a microprocessor that receives the second measurement signal and the second reference signal generated by the detector and calculates the concentration of the second chromophore therefrom.

10. The photometer of claim 8, wherein the first, second, third, fourth, fifth, sixth, seventh and eighth LEDs are arranged around a circle and are arranged in radially-aligned pairs, with the first and second LEDs being radially aligned, the third and fourth LEDs being radially aligned, the fifth and sixth LEDs being radially aligned and the seventh and eighth LEDs being radially aligned.

11. The photometer of claim 1, wherein the first and second axes also define third and fourth quadrants, which are arranged diagonal to each other, and wherein centers of the third and fourth LEDs are respectively arranged in the third and fourth quadrants.

12. The photometer of claim 1, wherein the first, second, third and fourth LEDs are arranged around a circle having a center at the intersection of the first and second axes.

13. The photometer of claim 12, wherein the first and second LEDs are radially aligned and wherein the third and fourth LEDs are radially aligned.

14. A method of measuring the concentration of a chromophore in a fluid, the chromophore absorbing light at a measurement wavelength and absorbing substantially less light at a reference wavelength, the method comprising:
    placing the fluid with the chromaphore in a sample cell through which an optical path extends;
    generating measurement light at the measurement wavelength from first and second light emitting diodes (LEDs) positioned diagonal to each other, the measurement light traveling along the optical path;
    generating reference light at the reference wavelength from third and fourth LEDs positioned diagonal to each other, the reference light traveling along the optical path;
    receiving the reference light after having passed through the sample cell containing the chromopore;
    receiving the measurement light after having passed through the sample cell containing the chromopore;
    generating a reference signal proportional to the intensity of the reference light received;
    generating a measurement signal proportional to the intensity of the measurement light received;
    determining the concentration of the chromophore from the measurement and reference signals; calculating an LED drift compensation factor at a time T1 before the step of placing the fluid with the chromaphore in the sample cell; measuring the time that has elapsed from time T1 to the time the concentration of the chromophore is determined; multiplying the LED drift compensation factor by the measured amount of elapsed time to produce a drift compensation; and applying the drift compensation to the determined concentration of chromophore.

15. The method of claim 14, wherein the step of generating the reference light is performed before the step of generating the measurement light.

16. The method of claim 14, wherein the step of calculating the LED drift compensation factor comprises:
    (a.) placing a zero sample fluid in the sample cell, the zero sample cell having no absorption at the measurement wavelength and no measurement at the reference wavelength;
    (b.) generating measurement light at the measurement wavelength from the first and second LEDs, the measurement light traveling along the optical path;
    (c.) generating reference light at the reference wavelength from the third and fourth LEDs positioned diagonal to each other, the reference light traveling along the optical path;
    (d.) receiving the reference light after having passed through the sample cell with the zero sample fluid disposed therein;
    (e.) receiving the measurement light after having passed through the sample cell with the zero sample fluid disposed therein;
    (f.) generating a measurement signal proportional to the intensity of the measurement light received;
    (g.) generating a reference signal proportional to the intensity of the reference light received;
    (h.) determining a first zero absorbance from the reference and measurement signals;
    (i.) after the elapse of a measurement time period, re-performing steps (a.) through (g.) and then determining a second zero absorbance from the reference and measurement signals;
    (j.) subtracting the first and second zero absorbances and dividing by the measurement time period to calculate a drift rate; and
    (j.) using the calculated drift rate to calculate the drift compensation factor.

17. The method of claim 14, wherein the chromophore is a first chromophore and wherein the method also measures the concentration of a second chromophore in the field, the second chromophore absorbing light at a second measurement wavelength and absorbing substantially less light at the reference wavelength, the method further comprising:
    generating second measurement light at the second measurement wavelength from fifth and sixth LEDs positioned diagonal to each other, the second measurement light traveling along the optical path;
    generating the reference light at the reference wavelength from the third and fourth LEDs, the reference light traveling along the optical path;
    receiving the reference light after having passed through the sample cell containing the second chromopore;
    receiving the second measurement light after having passed through the sample cell containing the second chromopore;
    generating a second reference signal proportional to the intensity of the reference light received;
    generating a second measurement signal proportional to the intensity of the second measurement light received; and
    determining the concentration of the second chromophore from the second measurement signal and the second reference signal.

* * * * *